United States Patent [19]

Sjöberg et al.

[11] Patent Number: 4,935,168
[45] Date of Patent: Jun. 19, 1990

[54] PROCESS FOR THE PREPARATION OF ALCOHOLS

[75] Inventors: Kjell Sjöberg, Stocksund; Björn åkermark, Saltsjöbaden, both of Sweden

[73] Assignee: Triple Crown Aktiebolag, Sweden

[21] Appl. No.: 356,579

[22] Filed: May 22, 1989

Related U.S. Application Data

[63] Continuation of Ser. No. 94,128, Sep. 8, 1987, abandoned.

[30] Foreign Application Priority Data

Sep. 12, 1986 [SE] Sweden .................................. 8603846

[51] Int. Cl.$^5$ ................................................ C07J 9/00
[52] U.S. Cl. .................................................... 552/545
[58] Field of Search ................................ 260/397.25

[56] References Cited

U.S. PATENT DOCUMENTS

| | | | |
|---|---|---|---|
| 2,410,590 | 11/1946 | Shantz | 260/397.25 |
| 2,835,682 | 5/1958 | Steiner et al. | 260/397.25 |
| 2,866,739 | 12/1958 | Ciesielski et al. | 260/397.25 |
| 3,840,570 | 10/1974 | Julian | 260/397.25 |
| 3,879,431 | 4/1975 | Clark et al. | 260/397.25 |
| 3,965,085 | 6/1976 | Holmbom et al. | 260/397.25 |
| 4,374,776 | 2/1983 | Struve et al. | 260/397.25 |
| 4,420,427 | 12/1983 | Hamunen | 260/397.25 |

FOREIGN PATENT DOCUMENTS 274237  6/1951  Switzerland .................. 260/397.25

OTHER PUBLICATIONS

Composition of Tall Oil Pitch, B. Holmbom, JACCS, 55, pp. 342-344, (1978).
Chemical Modification and Utilization of the Neutral Compounds in Mixed Birch-Pine Soap, Viljava et al., Paperi ja Puu, No. 12 (1985).
Tall Oil and Its Uses-II, E. E. McSweeney et al., Pulp Chemicals Association, Inc. New York City (1987).
Kaukas Woodbased Chemicals, OY Kaukas AB, Lappeenranta, Finland.

Primary Examiner—Joseph A. Lipovsky
Attorney, Agent, or Firm—Brumbaugh, Graves, Donohue & Raymond

[57] ABSTRACT

The present invention relates to a method to set free sterols from organic materials containing esters of such sterols, generally enriched distillation residues, or desodorisates by treating said organic material with ammonia and/or an amine and/or compound releases ammonia and/or amines while heated, the treament being carried out preferably at an elevated temperature, and under an elevated pressure.

5 Claims, No Drawings

PROCESS FOR THE PREPARATION OF ALCOHOLS

This application is a continuation of application Ser. No. 094,128, filed on 9/8/87, now abandoned.

DESCRIPTION

Technical Field

Sterols are alcohols used as starting materials in the manufacture of steroids or intermediates to biologically active steroids. They are present partly as esters in for instance distillation residues or so called desodorisates.

Isolation of sterols from these sources has so far been achieved either by alkaline hydrolysis or transesterification. A review has recently been published by A. Struwe et al in Fette, Seifen, Anstrichmitteln, 87, 103–106 (1985) and in DE-A1-2,936,125.

Both these methods have disadvantages that show up in the purification of the sterols. Addition of inorganic salts, i.e., sodium salts, to accomplish the hydrolysis or transesterification according to earlier methods makes it difficult to carry out extraction, crystallization, or distillation.

The transesterification is carried out with large molar excess of alkanol, leading to costly handling as well as too large distillation units for the recovery of alcanols, as well as to fire hazards, explosion risks, and environmental problems.

Thus a more simple and more rational process is desired.

An object of the present invention is to obtain a simple and rational process for the preparation of sterols from the mixtures containing sterols, and/or sterol derivatives so that they can readily be isolated by simple isolation processes known per se.

DESCRIPTION OF THE PRESENT INVENTION

It has now surprisingly turned out to be possible to overcome these difficulties by treating material that contains esters of sterols with ammonia, or different amines or compounds that liberate ammonia or amines when heated, e.g. urea. The method is thereby characterized by treatment of a product containing sterol esters with substantially equimolar amounts of ammonia and/or amine in relation to esters and acids present in the product, preferably at elevated temperature, and under elevated pressure.

By this method we obtain free sterols and amides of acids present. The free sterols can be isolated from the mixtures obtained by known methods. Suitable, but for the invention non-restricting raw materials containing sterols are different so called desodorisates, for instance, from soya, tall oil pitch, wool fat, some animal fats, gallic acids, coco oil, palm oil, tallow oil, where the sterols are present in concentrations of 1% or more.

Interesting sterols are, for example, stigmasterol, beta-sitosterol, campesterol, beta-sitostanol, cholesterol, and others.

Ammonia and different amines are, for example, primary, secondary, aliphatic, aromatic, araliphatic, cyclic, mono-, di-, tri-, or polyamines, as well as substituted amines can be used as well as compounds that liberate ammonia or amines at an elevated temperature, such as urea. Industrially ammonia, fatty amines or ethanol amines should be preferred.

The reaction is advantageously carried out at temperatures, where decomposition or rearrangement of the sterols is avoided, a temperature between about 100° C. and 250° C. is preferred. If the temperature is increased further, one has to check that the sterols are not damaged. The reaction can proceed with or without pressure. A solvent is generally not necessary. Water formed can, if needed, be removed under reduced pressure or by azeotropic distillation.

The reaction can be run batchwise or continuously.

The following amines are useful: primary amines such as methyl-, ethyl-, propyl-, butyl-, octyl-, 2-ethylhexylamine, lauryl-) tetradecyl-, cetyl-, octadecyl-, or fatty amines generally straight or with branched chains, cyclohexylamine, bensylamine, ethanolamine, propanolamine, aniline, substituted anilines, allylamine, hydroxyamine, etheramine as alcoxy propylamine.

Secondary amines are for example, dimethylamine, diethylamine, and so on with straight or branched chains being symmetric or asymmetric, morpholines, piperidines, diethanolamine, dicocoamine, secondary etheramines, or fatty acid alkylamines.

Diamines are, for example, hydrazine, ethylenediamines, laurylamineethylamine, piperazines. Triamines are diethylenetriamine, or polyamines.

Analysis method: The sample is treated with bis(-trimethylsilyl) trifluoroacetamide and chlorotrimethyl silane in methylene chloride in a tube with a tight fitting at 70° C. for 30 minutes. The sample is then analyzed by gas chromatography in a capillary column SE-30, 25 m long, phase thickness 0.25 $\mu$m id 0.32 mm. Cholesterol (99.5%, Merck) was used as internal standard.

EXAMPLE 1

Water was removed from 1 kg soybean desodorisate by simple distillation. 400 g of the residue were treated with 120 g of laurylamine (dodecylamine) at 200° C. for 18 hrs. The reaction was chosen with respect to the completeness of the liberation of sterols, where also the sensitivity to temperature of the sterol must be taken in consideration. After purification, we isolated 27 g of a mixture of sterols, mainly containing beta-sotosterol, campesterol, stigmasterol. Total contents of sterols in the product was about 90%.

EXAMPLE 2

400 g of pitch from tallow distillation were treated with 33 g of hydrazine hydrate in a three-necked flask provided with a stirrer at 108° C. for 22 hrs after which time period about 75% of the sterols present were free. After purification 18 g of a mixture of mainly cholesterol, sitosterol, campesterol, and stigmasterol were obtained. The total content of sterols in the product was about 85%.

EXAMPLE 3

To 80 g of pitch from "tall" oil distillation residue 3 g of ammonia were added in an autoclave, and the temperature was increased to and maintained at 150° C. for 6 hrs. After purification 6 g of mixture of beta-sitosterol, campesterol, and sitostanol having a purity of totally 86% of sterols, were obtained.

EXAMPLE 4

In a continuous pressure reactor preheated "tall" oil pitch was charged at a rate of 100 g per hour simultaneously with ammonia at a rate of 8 g per hr. The temperature was 210° C. and the residence time was varied from 30 min to 3 hrs related to desired turnover. Ammonia could be recycled, thus allowing a larger excess. A mixture containing typically 11–14% of free sterols was obtained. The mixture could be further purified to give a crystalline product of 80–90% purity.

EXAMPLE 5

We treated 400 g of "tall" oil pitch with monoethanolamine in a three-necked flask provided with a stirrer at 160° C. After 12 hrs 90% of the sterols were free. After purification we isolated 32 g of a mixture of beta-sitosterol, campesterol and sitostanol having about 90% purity.

EXAMPLE 6

75 g of a residue from fatty acid recovery were treated with 13 g of aniline at 200° C. for 24 hrs. After purification we isolated 3.0 g of a mixture of sterols in 90% purity.

EXAMPLE 7

100 g of a residue from fatty acid recovery were treated with 20 g of diethanolamine in a three-necked flask provided with a stirrer. After 13 hrs at 170° C. we obtained a product that, after purification, gave 11 g of sterols of 86% purity.

EXAMPLE 8

Water was evaporated from 1 kg of soya desodorisate by a simple distillation. 400 g of the residue were treated with 110 g of "lilamuls PG" (N-tallowpropylene diamine) at 170° C. for 18 hrs. The reaction time is chosen in relation to the desired percentage of sterols to set free. After purification we isolated a mixture of 27 g of sterols, mainly consisting of beta-sitosterol, campesterol, stigmasterol in totally 90% purity.

EXAMPLE 9

To 120 g of pitch from "tall" oil distillation were added 13 g of urea in an autoclave, and the temperature was increased to and maintained at 270° C. for 5 hrs. After purification 15.5 g of a mixture of beta-sitosterol, campesterol and sitostanol having a purity of total 82% of sterols were obtained.

We claim:

1. A process for the production of free sterols from tall oil pitch comprising sterol esters, said process comprising reacting tall oil pitch at an elevated temperature of about 150°–250° C. with a compound selected from the group consisting of ammonia, amines and compounds which liberate ammonia or amines at an elevated temperature and in an amount sufficient to cause free sterols to be liberated from the tall oil pitch.

2. The method according to claim 1, wherein the amine is selected from the group consisting of primary, secondary, aliphatic, aromatic, araliphatic, cyclic, mono-, di-, tri-, and polyamines.

3. The method according to claim 1, wherein the compound, is added to the reaction in an amount substantially equimolar in relation to acids and sterol esters present in the tall oil pitch.

4. The method according to claim 3, wherein the amount of compound added is at least equimolar in relation to acids and sterol esters present in the tall oil pitch.

5. The method according to claim 1, further comprising reacting tall oil pitch with the compound at an elevated pressure.

* * * * *